United States Patent [19]

Stein et al.

[11] 3,932,168

[45] Jan. 13, 1976

[54] SUBSTITUTED ARYLOXYACETAMIDO NITRILE DERIVATIVES AS CARBOHYDRATE DEPOSITION AGENTS

[75] Inventors: Robert George Stein, Kenosha, Wis.; Aldo Joseph Crovetti, Lake Forest, Ill.

[73] Assignee: Abbott Laboratories, North Chicago, Ill.

[22] Filed: Sept. 14, 1973

[21] Appl. No.: 397,533

Related U.S. Application Data

[63] Continuation-in-part of Ser. No. 200,263, Nov. 17, 1971, abandoned.

[52] U.S. Cl. .................... 71/105; 71/76; 260/464; 260/465 E; 260/465 D; 260/465.5
[51] Int. Cl.² .......................................... A01N 9/20
[58] Field of Search ...................... 71/105

[56] References Cited
UNITED STATES PATENTS

| | | | |
|---|---|---|---|
| 3,439,018 | 4/1969 | Brookes et al. | 260/465 D |
| 3,556,762 | 1/1971 | Hamm | 71/76 |
| 3,557,209 | 1/1971 | Richter et al. | 260/465 D |
| 3,635,692 | 1/1972 | Breuer | 71/118 |

*Primary Examiner*—Glennon H. Hollrah
*Attorney, Agent, or Firm*—Robert L. Niblack; James L. Bailey; Vincent A. Mallare

[57] ABSTRACT

Covers substituted aryloxyacetamido nitrile derivatives having the following general formula:

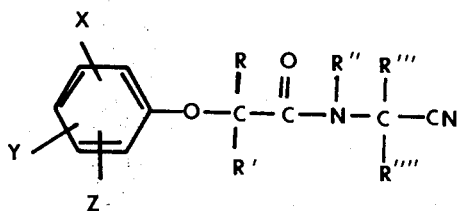

wherein X, Y and Z are selected from the group consisting of hydrogen, loweralkyl and halo, R and R' are selected from the group consisting of hydrogen and loweralkyl, R'', R''' and R'''' are selected from the group consisting of hydrogen, loweralkyl, alkenyl, alkynyl, aryl, substituted aryl, and benzyl and R''' and R'''' when taken together are cycloalkane, which derivatives are useful in increasing carbohydrate deposition in plants such as sugar cane.

3 Claims, No Drawings

SUBSTITUTED ARYLOXYACETAMIDO NITRILE DERIVATIVES AS CARBOHYDRATE DEPOSITION AGENTS

REFERENCE TO RELATED APPLICATION

This application is a continuation-in-part of our copending application, dated Nov. 17, 1971, bearing Ser. No. 200,263 now abandoned.

BACKGROUND OF THE INVENTION

Considerable research effort has been expended in developing compounds which are useful in influencing the growth and development of a wide variety of plants. One of the specific aims in such broad endeavors is to develop a series of compounds which can benefit useful plants such as sugar cane by increasing sucrose content via treatment with chemical compounds.

It therefore becomes an object of the invention to provide a class of compounds which influence the growth and development of a wide variety of plant species.

A specific object of the invention is to provide a group of compounds which increase carbohydrate deposition in a variety of useful plants.

A particular object of the invention is to provide a method of increasing sucrose content in plants such as sugar cane via treatment with a broad class of compounds.

Other objects will appear hereinafter.

SUMMARY OF THE INVENTION

In accordance with the invention a class of nitrile compounds has been discovered which can be used to benefit useful plants by increasing carbohydrate deposition. These substituted aryloxyacetamido nitrile derivatives have the following general formula:

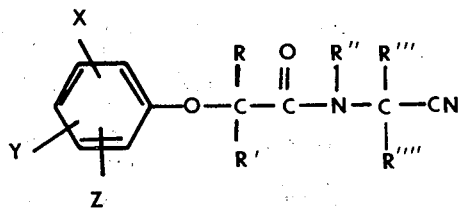

wherein X, Y and Z are selected from the group consisting of hydrogen, loweralkyl and halo, R and R' are selected from the group consisting of hydrogen and loweralkyl, R'', R''' and R'''' are selected from the group consisting of hydrogen, loweralkyl, alkenyl, alkynyl, aryl, substituted aryl and benzyl, and R''' and R'''' when taken together are cycloalkane. In a greatly preferred embodiment, the herewith described compounds are used to treat sugar cane to increase the sucrose yield in the sugar cane.

DETAILED DESCRIPTION OF THE INVENTION

The compounds described here may be prepared via a variety of synthetic techniques. However, the following is a preferred synthetic route due to ease of reaction and excellent overall yields.

Essentially, the substituted aryloxyacetamido nitrile derivatives are prepared by first reacting a ketone or aldehyde with HCN and an amine to produce an aminoacetonitrile. The aminoacetonitrile in turn is reacted with an unsubstituted, halo substituted, or loweralkyl substituted phenoxyacetyl chloride, The phenoxyacetyl chloride is generally prepared by refluxing the parent acid with thionylchloride in a solvent such as benzene for several hours. Thereafter, the solution is concentrated to an oil and distilled under reduced pressure to produce a purified phenoxyacetyl chloride. This procedure is set out in J. Am. Chem. Soc. 68, 2112 (1946).

The phenoxyacetyl chloride is then reacted with a wide variety of amino nitriles to produce the corresponding amido nitrile.

The following lists typical amino nitriles used to make the corresponding amido nitriles.

TABLE I

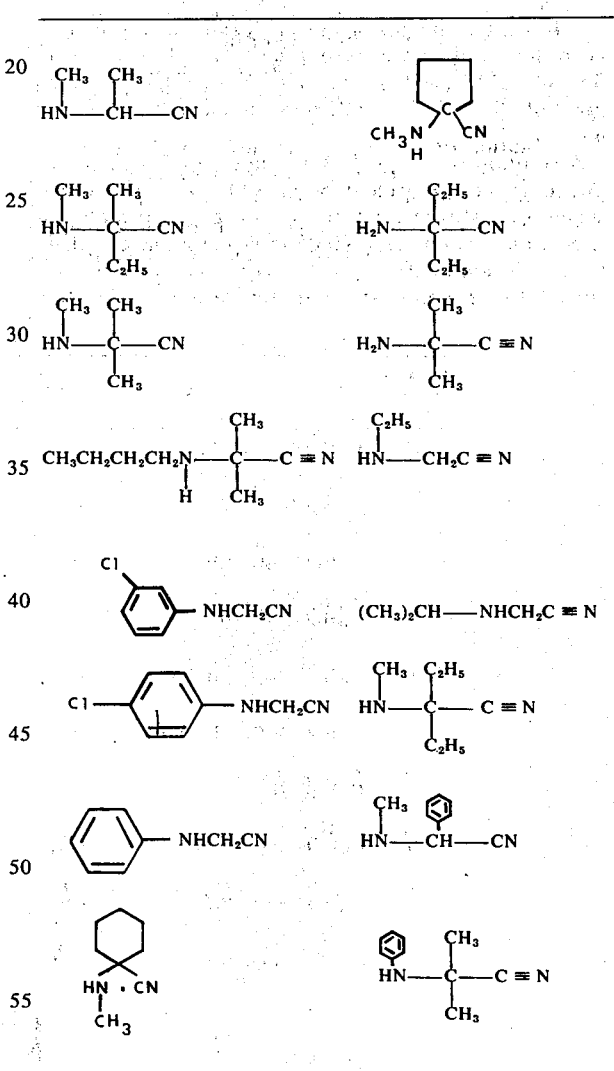

In more detail, in order to prepare the amido nitriles the following general procedure is carried out:

A solution of the halo substituted, loweralkyl substituted or unsubstituted phenoxyacetyl chloride (1 equivalent) in benzene is added to a stirred solution of 1 equivalent of the aminoacetonitrile derivative and 1 equivalent triethylamine. The triethylamine is employed as an acid acceptor and other equivalent acid acceptors such as picolines, triethylamine, morpholine, pyridine, etc. may be employed. Likewise, the reaction solvent may be other than benzene such as ether, chloroform, methylene chloride, etc. If an aminoacetonitrile salt is used it is necessary to employ two equivalents of acid acceptor. AFter the solution is stirred several hours it is washed successively with water, dilute alkali, water again, dilute acid and finally water. It is then subsequently dried over a dessicant such as magnesium sulfate. The drying agent is removed and the filtrate is concentrated under vacuum to give the desired product.

The following examples illustrate typical useful compounds of the invention and their method of preparation:

EXAMPLE I

N-Cyanomethyl 2,4-Dichlorophenoxyacetamide 2,4-Dichlorophenoxyacetyl chloride was prepared according to the procedure described in J. Am. Chem. Soc. 68, 2112 (1946). The acid chloride had a boiling point of 155°–157° C. at 22 mm., and a melting point of 44°–45° C.

A solution of 11.95 g. (0.05 mole) of 2,4 dichlorophenoxyacetyl chloride in 50 ml. of benzene was added slowly to a stirred mixture of 10.1 g. (0.10 mole) of triethylamine and 4.2 g. (0.05 mole) aminoacetonitrile hydrochloride in 200 ml. of benzene. The mixture was stirred for 2 hours at room temperature and then washed successively with water, 5% sodium hydroxide solution, water, 5% hydrochloric acid solution, and water and then dried over magnesium sulfate. The resultant filtrate was concentrated under vacuum to give a solid which was crystallized from dilute ethanol to give 8.6 g. (66% yield) of product having a melting point of 107°–108° C.

A number of other compounds were prepared according to the procedure just described by reacting 2,4-dichlorophenoxyacetyl chloride with a variety of aminonitriles. These compounds have the following general formula:

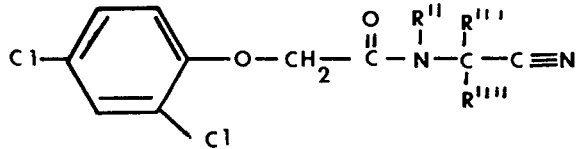

where R', R''' and R'''' are radicals as previously defined.

Table II below sets out the physical constants and analyses of these compounds.

TABLE II

| Example Number | Formula | R'' | R''' | R'''' | Melting Point | Analyses C | H | Theoretical Found N |
|---|---|---|---|---|---|---|---|---|
| 2 | C₁₁H₁₀Cl₂N₂O₂ | CH₃ | H | H | 136–137 | 48.37<br>48.41 | 3.69<br>3.82 | 10.25<br>10.25 |
| 3 | C₁₂H₁₂Cl₂N₂O₂ | C₂H₅ | H | H | 93–94 | 50.20<br>50.27 | 4.21<br>4.25 | 9.76<br>9.84 |
| 4 | C₁₂H₁₂Cl₂N₂O₂ | CH₃ | H | CH₃ | 103–104 | 50.20<br>50.41 | 4.21<br>4.22 | 9.76<br>9.94 |
| 5 | C₁₂H₁₂Cl₂N₂O₂ | H | CH₃ | CH₃ | 154–156 | 50.20<br>49.97 | 4.21<br>4.20 | 9.76<br>9.91 |
| 6 | C₁₃H₁₄Cl₂N₂O₂ | CH(CH₃)₂ | H | H | 69–71 | 51.84<br>51.91 | 4.68<br>4.70 | 9.30<br>9.42 |
| 7 | C₁₃H₁₄Cl₂N₂O₂ | CH₂CH₂CH₃ | H | H | *180–185/3 | 51.84<br>51.71 | 4.68<br>4.86 | 9.30<br>9.26 |
| 8 | C₁₃H₁₄Cl₂N₂O₂ | CH₃ | CH₃ | CH₃ | 129–130 | 51.84<br>51.80 | 4.68<br>4.80 | 9.30<br>9.32 |
| 9 | C₁₄H₁₆Cl₂N₂O₂ | C₂H₅ | CH₃ | CH₃ | 98–99 | 53.35<br>53.18 | 5.11<br>5.19 | 8.88<br>8.87 |
| 10 | C₁₄H₁₆Cl₂N₂O₂ | CH₃ | CH₃ | C₂H₅ | 104–105 | 53.35<br>53.15 | 5.11<br>5.12 | 8.88<br>8.84 |
| 11 | C₁₄H₁₆Cl₂N₂O₂ | H | C₂H₅ | C₂H₅ | 116–117 | 53.35<br>53.63 | 5.11<br>5.26 | 8.88<br>9.00 |
| 12 | C₁₅H₁₆Cl₂N₂O₂ | CH₃ | ⌬ (cyclopentyl) | | 90–92 | 55.06<br>55.26 | 4.92<br>4.97 | 8.55<br>8.58 |
| 13 | C₁₅H₁₈Cl₂N₂O₂ | CH₃ | C₂H₅ | C₂H₅ | 114–115 | 54.72<br>54.77 | 5.51<br>5.67 | 8.50<br>8.69 |
| 14 | C₁₅H₁₈Cl₂N₂O₂ | CH₂CH₂CH₃ | CH₃ | CH₃ | 104–105 | 54.72<br>55.03 | 5.51<br>5.67 | 8.50<br>8.67 |
| 15 | C₁₆H₁₁Cl₃N₂O₂ | –C₆H₄–Cl | H | H | 106–107 | 51.99<br>52.12 | 2.99<br>3.01 | 7.57<br>7.76 |
| 16 | C₁₆H₁₁Cl₃N₂O₂ | –C₆H₄(Cl) | H | H | 117–118 | 51.99 | 2.99 | 7.57 |

TABLE II-continued

| Example Number | Formula | R″ | R‴ | R⁗ | Melting Point | Analyses C | H | Theoretical Found N |
|---|---|---|---|---|---|---|---|---|
| | | | | | | 52.20 | 3.02 | 7.73 |
| 17 | $C_{16}H_{12}Cl_2N_2O_2$ | H | H |  | 121–122 | 57.33<br>57.76 | 3.60<br>3.64 | 8.35<br>8.43 |
| 18 | $C_{16}H_{12}Cl_2N_2O_2$ |  | H | H | 89–90 | 57.33<br>57.62 | 3.60<br>3.64 | 8.35<br>8.54 |
| 19 | $C_{16}H_{18}Cl_2N_2O_2$ | $CH_3$ |  | | 129–130 | 56.32<br>55.91 | 5.31<br>5.66 | 8.20<br>7.91 |
| 20 | $C_{16}H_{20}Cl_2N_2O_2$ | $CH_2CH_2CH_2CH_3$ | $CH_3$ | $CH_3$ | 90–91 | 55.99<br>56.07 | 5.87<br>5.92 | 8.15<br>8.30 |
| 21 | $C_{17}H_{14}Cl_2N_2O_2$ | $CH_3$ | H |  | 99–100 | 58.47<br>58.44 | 4.04<br>4.07 | 8.01<br>8.06 |
| 22 | $C_{18}H_{16}Cl_2N_2O_2$ | $CH_3$ | H |  | 94–95 | 59.52<br>59.64 | 4.43<br>4.46 | 7.70<br>7.81 |
| 23 | $C_{18}H_{16}Cl_2N_2O_2$ |  | $CH_3$ | $CH_3$ | 117–118 | 59.53<br>59.32 | 4.43<br>4.41 | 7.70<br>7.74 |

*Boiling Point

The active ingredient may be utilized in diverse formulations, including the adjuvants and carriers normally employed for facilitating the dispersion of active ingredients for agricultural applications. Thus, the just-described nitrile derivatives may be formulated as a solution or dispersion, in aqueous or nonaqueous media, as a powdery dust, as a wettable powder, as an emulsifiable concentrate, as a granule, or as any of several other known types of formulations. These growth regulatory compositions may be applied as sprays, dips, dust, or granules to the plant situs. These formulations may contain as little as 0.0005% or as much as 95% or more by weight of active ingredient, and applications may be at rates equivalent to less than 2 to over 400 lbs./acre, more often 2 – 100 lbs./acre.

In order to provide compositions in the form of dusts, high-strength concentrates, granules, pellets, water-dispersible powders, aqueous solutions, dispersions, or emulsions and solutions or dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared a conditioning agent comprising one or more surface-active agents or surfactants is present in amounts sufficient to render a given composition containing the active compounds readily dispersible in water or in oil.

The surface active agent used in the invention here can be a wetting, dispersing or emulsifying agent which will assist dispersion of the compound. The surface-active agent or surfactant can include such anionic, cationic and nonionic agents as have heretofore been generally employed in plant control compositions of similar type. Suitable surface-active agents are set forth, for example, in "Detergents and Emulsifiers" 1971 Annual by John W. McCutcheon, Inc.

In general, less than 10% by weight of the surface-active agent will be used in compositions of this invention, and ordinarily the amount of surface-active agent will range from 1 – 5% but may even be less than 1% by weight.

Additional surface-active agents can be added to the formulations to increase the ratio of surfactant:active ingredient up to as high as 5:1 by weight. Such compositions may have a greater biological effectiveness than can be expected from a consideration of the activity of the components used separately. When used at higher rates, it is preferred that the surfactant be present in the range of one-fifth to five parts surfactant for each one part of active agent.

WETTABLE POWDERS

Wettable powders are water-dispersible compositions containing the active material, an inert solid extender, and one or more surfactants to provide rapid wetting and prevent heavy flocculation when suspended in water.

The inert extenders which are preferred for use in the wettable powders of this invention containing the active compounds are of mineral origin.

The classes of extenders suitable for the wettable powder formulations of this invention are the natural clays, diatomaceous earth and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Among the more preferred surfactants are the nonionic and anionic types, and those most suitable for the preparation of the dry, wettable products of this invention are solid forms of compounds known to the art as wetters and dispersants. Occasionally a liquid, nonionic compound classified primarily as an emulsifier may serve as both wetter and dispersant.

Most preferred wetting agents are alkylbenzene and alkylnapthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium napthalene sulfonates, polymethylene bis-napthalene sulfonate, and sodium-N-methyl-N-(long chain acid) tautrates.

Wetting and dispersing agents in these preferred wettable powder compositions of the invention are usually present at concentrations of from about 0.5 weight percent to 5 weight percent. The inert extender then completed the formulation.

Thus, wettable powder formulations of the invention will contain from about 25 to 90 weight percent active material, from 0.5 to 2.0 percent wetting agent, from 0.25 to 5.0 weight percent dispersant, and from 9.25 to 74.25 weight percent inert extender, as these terms are described above.

HIGH-STRENGTH COMPOSITIONS AND AQUEOUS SUSPENSION CONCENTRATES

High-strength compositions generally consist of 90 to 99.5 percent active ingredient and 0.5 to 10 percent of a liquid or solid surfactant such as those described in "Detergents and Emulsifiers" 1971 Annual by John W. McCutcheon, Inc. Such high-strength compositions can often be used in a manner similar to the wettable powders but they are also suitable for further formulation.

The aqueous suspension concentrates are prepared by mixing together and sand grinding an aqueous slurry of water-insoluble active ingredient in the presence of dispersing agents until a concentrated aqueous slurry is obtained in which the particles of active ingredient are substantially all below 5 microns in size. This concentrated aqueous suspension is characterized by its extremely small particle size so that upon diluting and spraying, a very uniform coverage is obtained.

These just-described aqueous suspension concentrates will contain from 15 to 40% of active ingredient, from 45 to 70% water, with the remainder made up of surfactants, corrosion inhibitors and suspending agents.

Suspensions in organic liquids can be prepared in a similar manner such as by replacing the water with mineral oil.

DUSTS

Dusts are dense powder compositions which are intended for application in dry form. Dusts are characterized by their free-flowing and rapid settling properties so that they are not readily windborn to areas where their presence is not desired. They contain primarily an active ingredient and a dense, free-flowing, solid extender. Their performance is sometimes aided by the inclusion of a wetting agent, and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and antifoam agents may also be found as component of a dust.

Thus, the dust compositions of this invention will comprise from about 5 to 20 weight percent active ingredient, 5 to 25 weight percent filler, 0 to 1.0 weight percent wetting agent and from about 30 to 90 weight percent dense, free-flowing extender, as these terms are used herein.

EMULSIFIABLE OILS

Emulsifiable oils are usually solutions of active material in nonwater miscible solvents together with a surfactant.

For the compounds of this invention, emulsifiable oils can be made by mixing the active ingredient with a solvent and surfactant. Suitable solvents for the compound of this invention are chlorinated solvents, nonwater miscible ethers, esters, or ketones alone or in admixture with aromatic hydrocarbons. Suitable surfactants are those ionic or nonionic agents known to the art as emulsifying agents.

Emulsifying agents most suitable for the emulsifiable oil compositions of this invention are long-chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates or, preferably mixtures of these emulsifying agents. Such emulsifying agents will comprise from about 1 to 10 weight percent of the total composition. As described above, however, up to 5 parts of emulsifying agent for each part of active ingredient can be used.

Thus, emulsifiable oil compositions of the present invention will consist of from about 10 to 50 weight percent active ingredient, about 40 to 82% solvents, and about 1 to 10 weight percent emulsifier, as these terms are defined and used above.

In some instances the oil solution may be intended merely for extension with other oils, and in this instance, the emulsifying agent may be omitted and may be replaced by additional solvent.

GRANULES AND PELLETS

Granules and pellets are physically stable, particulate compositions containing a compound of this invention which adheres to or is distributed through a basic matrix of a coherent, inert carrier with microscopic dimensions. In order to aid leaching of the active ingredient from the granule or pellet, a surfactant can be present.

The inert carrier is preferably of mineral origin, and suitable carriers are natural clays, some pyrophyllites and vermiculite. Suitable wetting agents are anionic or nonionic.

For the granule compositions of this invention, most suitable carriers are of two types. The first are porous, absorptive preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite or bentonite clays in the form of sodium, calcium or magnesium bentonites. Water-soluble salts such as sodium salts may also be present to aid in the disintegration of the granules or pellets in the presence of moisture. These ingredients are blended with the active components to give mixtures that are granulated or pelleted, followed by drying to yield formulations with the active component distributed uniformly throughout the mass. Such granules or pellets can also be made with 25 to 30 weight percent active components but more frequently a concentration of about 10 weight percent is desired for optimum distribution. The granular compositions of this invention are most useful in a size range of 15 – 30 mesh.

The most suitable wetting agents for the granular compositions of this invention depend upon the type of granule used. When preformed granules are sprayed with active material in liquid form, the most suitable wetting agents are nonionic, liquid wetters miscible with the solvent. These are more generally known to the art as emulsifiers and comprise alkylaryl polyether alcohols, alkyl polyether alcohols, polyoxyethylene sorbitan fatty acid esters, polyethylene glycol esters with fatty or rosin acids, fatty alkylol amide condensates, oil soluble petroleum or vegetable oil sulfonates, or mixtures of these. Such agents will usually comprise up to about 5 weight percent of the total composition.

When the active ingredient is first mixed with a powdered carrier and subsequently granulated or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular pelleted formulations of this invention comprise about 5 to 30 weight percent active material, about 0 to 5 weight percent wetting agent, and about 65 to 95 weight percent inert mineral carrier, as these terms are used herein.

AQUEOUS SOLUTIONS

Certain compounds of this invention are soluble in mild acid or alkaline solutions and can be formulated and applied in aqueous solution in concentrations up to about 20%.

As noted above the compounds here have been found to promote a modification or alteration to the normal sequential development of plants to agricultural maturity. For example, in carbohydrate depositing plants, the application of the compounds of this invention leads to an earlier deposition of the carbohydrate and usually in a greater amount. Thus, through the application of the compounds of this invention, this "maximum" deposition period can be advanced in the maturity cycle. Such plant species as Irish potatoes, sweet potatoes, sugar beets, sugar cane, grapes, melons, silage crops, and citrus and other tree fruits show an earlier accumulation of carbohydrates upon application to this plant species of a compound or combination of compounds of this invention.

The compounds have shown particular activity in controlling the maturation and sucrose accumulation in growing sugar cane. It appears that application to the upper portion of the sugar cane plant particularly the leaves and growing point (spindle area), of the compounds here several weeks before harvest leads to suppression of the terminal growth of the sugar cane, thereby, in effect, inducing an early ripening of the sugar cane and thus increasing the sucrose content of the sugar cane. It also appears that various carbohydrates in the plant are converted to sucrose, leading to a significant increase in the total yield of sucrose in the plant.

The compounds of the present invention are applied to the tops of growing sugar cane, preferably about two to ten weeks before harvesting time by any of the usual means well known in the art, for instance, by appropriately spraying them in the form of an aqueous solution containing one or more of the above-discussed surfactants in order to provide more effective wetting of the plant. The spraying can be accomplished either by mechanical or hydraulic agricultural sprayers, or alternately from an airplane, the exact mode depending upon the size of the area to be sprayed. Yields of sucrose from sugar cane so treated, are considerably increased as compared to those obtained from nontreated sugar cane.

The compounds can also be applied to the sugar cane in any of the forms discussed above.

The amount of compound applied to the sugar cane normally varies from about two to about ten pounds per acre.

As noted above, the compounds of the present invention are usually applied to the growing sugar cane about two to ten weeks before harvest, and preferably about four to five weeks before harvest.

In order to demonstrate the efficacy of the invention in this area, individual sugar cane stalks were treated with representative compounds several weeks before harvest. To avoid sampling errors, older cane, preferably 13 to 23 months old were employed in the test. In order to improve the accuracy of the analyses, only the terminal 15 joints of each stalk were used. An identical number of untreated sugar cane stalks, of the same age, were similarly processed to provide a control. A comparison of the values obtained for the treated cane provides with the control sample a convenient means of determining the effectiveness of these compounds as ripening agents.

The analyses are carried out by the press method of cane analyses, developed by T. Tanimoto and reported in Hawaiian Planters' Record, Vol. 57, p. 133. The data is expressed as juice purity and pol percent cane. Pol percent cane is a polarimetric determination and will equal the percentage of sucrose if it is the only substance in the solution which will rotate the plane of polarized light. In any event the determination of pol percent is considered by those skilled in the art as an effective means of determining the sucrose content of sugar cane juice.

In the first series of tests, about four weeks before harvesting, a number of compounds of the invention were applied in solution form to the tips of each of ten 23 month old sugar cane stalks. Table III which gives the results of these tests shows that application of these compounds resulted in a very substantial improvement in both juice purity and pol percent cane. The compound number in each case corresponds to the example number of the compounds shown in Table II as well as in Example I.

TABLE III

| Compound No. | Juice Purity | Pol Percent |
|---|---|---|
| 1 | 74.1 | 7.4 |
| 7 | 72.8 | 7.8 |
| 8 | 81.7 | 10.2 |
| 9 | 77.3 | 9.2 |
| 10 | 74.8 | 8.1 |
| 14 | 73.4 | 7.8 |
| Control | 73.7 | 7.7 |

A still further group of compounds were tested by applying them five weeks before harvest. Results are shown in Table IV below.

TABLE IV

| Compound No. | Juice Purity | Pol Percent |
|---|---|---|
| 2 | 71.7 | 9.5 |
| 4 | 82 | 11.4 |
| 5 | 79.3 | 12.1 |
| 15 | 72.9 | 8.9 |
| 16 | 73.8 | 8.9 |
| 18 | 76.3 | 10.0 |
| Control | 73.2 | 8.3 |

In the last series of the testing, still further compounds were tested by applying them five weeks before harvest. Results are given in Table V which again demonstrates the increase in juice purity and pol percent gain via application of the herewith described compounds.

TABLE V

| Compound No. | Juice Purity | Pol Percent |
|---|---|---|
| 1 | 78.9 | 10.5 |
| 9 | 75.6 | 9.7 |
| 10 | 75.3 | 10.9 |
| 11 | 74.5 | 9.5 |
| 14 | 79.5 | 10.5 |
| 20 | 79.6 | 9.7 |
| Control | 73.6 | 8.8 |

We claim:

1. A method of increasing carbohydrate deposition in plants which comprises applying to the maturing plant 2 to 10 weeks before harvest thereof an effective amount of a compound of the formula:

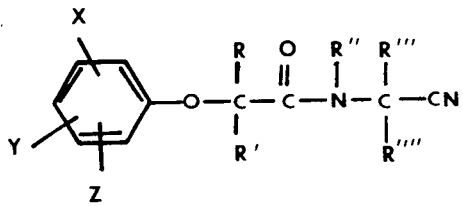

wherein X, Y and Z are selected from the group consisting of hydrogen, loweralkyl and chloro, R, R', R'', R''' and R'''' are selected from the group consisting of hydrogen and loweralkyl.

2. A method for accelerating the maturation of and sucrose accumulation in growing sugar cane which comprises application to the tops of the growing cane 2 to 10 weeks before harvest thereof an effective amount of a compound having the formula:

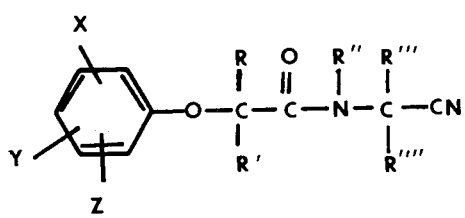

where X, Y and Z are selected from the group consisting of hydrogen, loweralkyl and chloro, R, R', R'', R''' and R'''' are selected from the group consisting of hydrogen and loweralkyl.

3. The method of claim 2 wherein R'' is H, R''' is $CH_3$ and R'''' is H.

* * * * *